United States Patent [19]

Filipi

[11] Patent Number: 4,505,414
[45] Date of Patent: Mar. 19, 1985

[54] EXPANDABLE ANVIL SURGICAL STAPLER
[76] Inventor: Charles J. Filipi, 1337 Sturm, Walla Walla, Wash. 99362
[21] Appl. No.: 541,155
[22] Filed: Oct. 12, 1983
[51] Int. Cl.³ .............................................. A61B 17/04
[52] U.S. Cl. ................................ 227/19; 128/334 R; 227/DIG. 1; 227/155
[58] Field of Search ..................... 128/334 R, 334 C; 227/DIG. 1, 19, 156, 152, 154, 155

[56] References Cited
U.S. PATENT DOCUMENTS

| | | | |
|---|---|---|---|
| 3,472,230 | 10/1969 | Fogarty | 128/345 X |
| 3,495,586 | 2/1970 | Regenbogen | 128/345 X |
| 3,519,187 | 7/1970 | Kapitanov et al. | 227/DIG. 1 |
| 3,908,662 | 9/1975 | Razgulov | 128/334 R |
| 4,007,743 | 2/1977 | Blake | 128/334 C X |
| 4,198,982 | 4/1980 | Fortner et al. | 227/DIG. 1 |
| 4,310,115 | 1/1982 | Inoue | 128/334 R X |
| 4,425,908 | 1/1984 | Simon | 128/345 X |

Primary Examiner—Paul A. Bell
Attorney, Agent, or Firm—Wells, St. John & Roberts

[57] ABSTRACT

Disclosed is an expandable anvil surgical stapler which can be collapsed and inserted through a small hole in a patient's body and also through a small hole formed in the side of a hollow organ. The stapler is equipped with an anvil which can be expanded outwardly after placement inside the patient's body. Staples are then driven through the tissue layers to securely fasten the wall of the organ to the abdominal wall or other external tissue layer of the patient's body. This rigid attachment of the organ to the abdominal wall allows subsequent surgical procedures to be performed without large incisions and without constant surgical assistance to maintain proper access to the interior of the organ.

7 Claims, 8 Drawing Figures

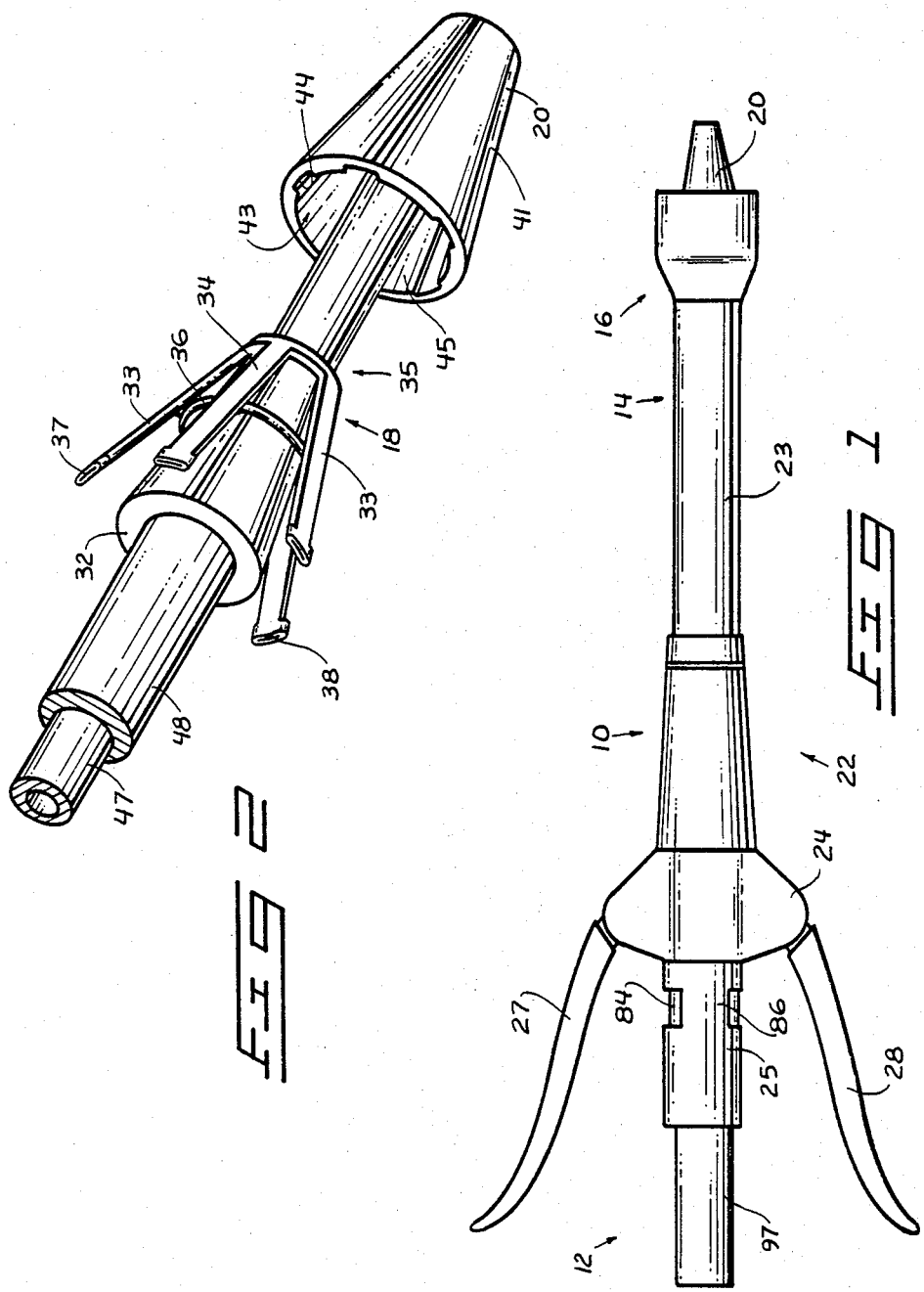

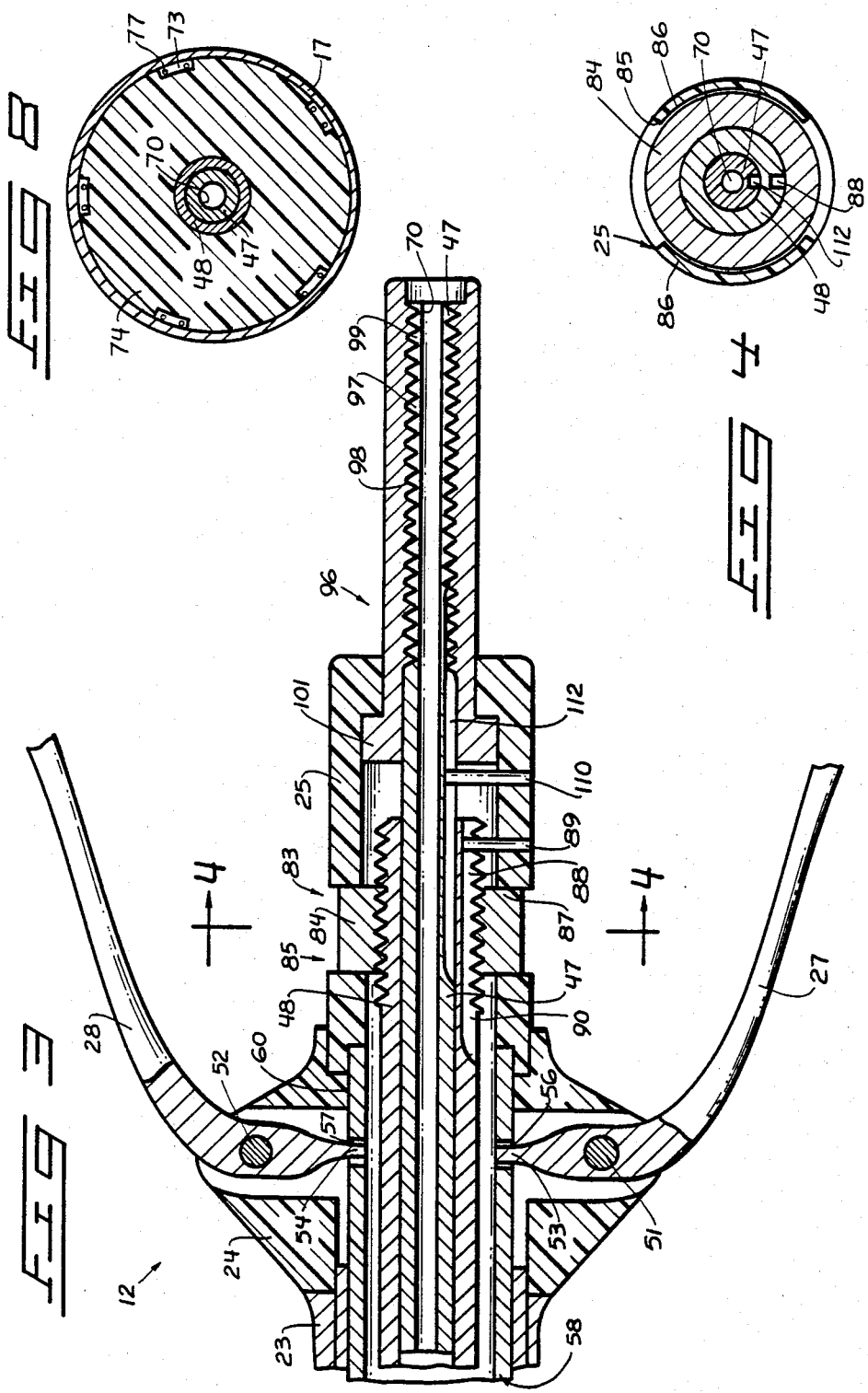

4,505,414

EXPANDABLE ANVIL SURGICAL STAPLER

TECHNICAL FIELD

The technical field of this invention is surgical stapling apparatus.

BACKGROUND

There are many surgical procedures which require access to internal organs of humans and animals. Common surgical techniques used in the past have involved making large incisions to gain access to internal organs. Of particular importance are organs, also known as viscus, which are contained within the peritoneal cavity. Viscus such as the stomach, small intestine and, gall bladder are typically accessed by making a large incision in the abdominal wall.

In recent years, experimentation with much smaller surgical incision has indicated that the risk of patient trauma and death are greatly reduced when compared to traditional large incisions. Unfortunately, in many cases it has been very difficult to obtain and maintain proper surgical access to the organ being operated upon when only a small incision is made.

The present invention provides an apparatus for stapling two layers of body tissue together to form a very small surgical opening. A typical use is to attach the abdomen or other body wall to a hollow organ to provide direct access to the inside of the hollow organ. The size of the opening necessary to gain access to the interior of the hollow organ is greatly reduced and therefore is much less susceptible to creating trauma in the patient.

The prior art relevant to this application includes end-to-end anastomosis devices used to staple the ends of a severed bowel back together. Such devices use a circular row of staples which are driven against an adjustably positioned end piece containing an anvil. The staples are driven through the bowel tissue and bent when they engage the anvil to thereby secure the ends of the bowel together.

BRIEF DESCRIPTION OF THE DRAWINGS

A preferred embodiment of this invention is illustrated in the accompanying drawings, in which:

FIG. 1 is a side elevational view showing an expandable anvil surgical stapler according to this invention;

FIG. 2 is an isometric view of the embodiment of the anvil and nosepiece included in the stapler of FIG. 1;

FIG. 3 shows a partial cross-sectional side view of the handle end of the stapler;

FIG. 4 is a cross-sectional view taken along line 4—4 of FIG. 3;

FIG. 8 is a cross-sectional view of the staple head taken at line 8—8 of FIG. 5;

DETAILED DESCRIPTION OF THE PREFERRED EMBODIMENTS

Figure 5:
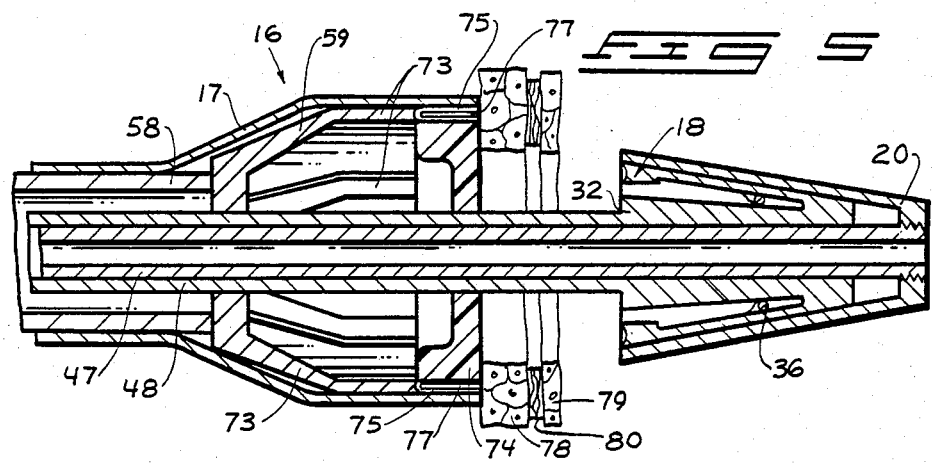
FIG. 5 shows a partial cross-sectional view of the stapler head and the expandable anvil positioned after insertion through the abdominal wall and layer of organ tissue.

In compliance with the constitutional purpose of the Patent Laws "to promote the progress of science and useful arts" (Article 1, Section 8), applicant submits the following disclosure of the invention.

FIG. 1 shows the overall expandable anvil surgical stapler of this invention. The surgical stapler 10 has a handle end 12 and a staple end 14. Staple end 14 includes a staple driver assembly 16 which holds and drives staples. Staple end 14 also includes an expandable anvil 18 (FIG. 2) and a means for collapsing and expanding the anvil such as nosepiece 20. Nosepiece 20 also serves to cover the anvil during insertion into a patient's body.

Surgical stapler 10 includes a frame 22 which forms the basic rigid structure of the tool. Frame 22 can be comprised of a single piece or a plurality of pieces which are joined together in a fixed relationship. In the preferred embodiment, frame 22 includes a barrel 23, central 24, and tailpiece 25. These pieces are joined together to form frame 22.

Handles 27 and 28 are pivotably connected to frame 22 for operating the staple driver assembly 16 when the handles are squeezed inwardly. Nut 84 and operator cylinder 97 are used to operate the expandable anvil and nosepiece in a manner which will be described below.

The preferred forms of expandable anvil 18 and nosepiece 20 are shown in isometric view of FIG. 2. Expandable anvil 18 includes an anvil body 32 which is slidably mounted upon catheter tube 47. Connected to the anvil body are a plurality of anvil struts 33. The anvil struts 33 are connected to anvil body 32 by hinged connections 34 at the forward end 35 of anvil 18. A strut biasing means such as wire spring 36 is provided to bias the anvil struts 33 outwardly into an expanded position such as shown in FIG. 2.

Anvil 18 also includes anvil heads 37 which preferably include crimping recesses 38 on the faces of the anvil heads for engaging and crimping the staples.

Expandable anvil 18 can be diminished in cross-sectional size by collapsing the anvil struts 33 inwardly against anvil body 32. FIG. 3 shows the preferred means for adjustably moving the anvil heads using nosepiece 20. Nosepiece 20 is provided with sloping exterior surfaces 41 which allow the nosepiece and enclosed anvil to be inserted through a relatively small opening in the tissue of a person being operated upon. The rear end of nosepiece 20 has a receiving cup 43 which is properly sized and shaped to receive the expandable anvil 18 thereinto. The receiving cup shown in FIG. 2 includes beveled interior surfaces 45 which converge inwardly. Grooves 44 can also advantageously be included on the interior surfaces 45 to more specifically guide and align the anvil struts 33 when the anvil is inserted into receiving cup 43.

Expandable anvil 18 and nosepiece 20 are preferably connected to frame 22 in a manner which allows independent relative motion between them and the frame. This can advantageously be accomplished by having the nosepiece 20 attached to a nosepiece connection means such as hollow tubular catheter guide 47. Tubular catheter guide 47 extends through frame 22 and is extended or retracted longitudinally into or out of the staple end of the frame by turning operator cylinder 97.

Anvil 18 is slidably positioned over the hollow tubular catheter guide 47 thereby keeping it in constant coaxial alignment but allowing it to move in and out of the receiving cup 43. Anvil 18 is preferably connected to an anvil connection means 48 which preferably is a cylindrical tubular member but which can also be a small actuating rod or plurality of rods disposed about catheter guide 47. The anvil connection means 48 is moved longitudinally up and down frame 22 using an anvil translation operator which will be described more fully below.

FIG. 3 shows the handle end 12 of frame 22. Barrel portion 23 is securely mounted in the front end of central portion 24 and the tailpiece 25 is mounted in the rear end of central portion 24. Handles 27 and 28 are pivotally connected to frame central portion 24 at pivots 51 and 52. Handles 27 and 28 have actuating tips 53 and 54 which extend into openings 56 and 57, respectively. Openings 56 and 57 are on opposed sides of the staple driver connector 58 which is slidable within frame 22. Staple driver connector 58 is maintained in position within frame 22 by the inside of barrel 23 and by boss 60 near the rear of frame central piece 24. Staple driver connector 58 presses upon staple driver 59 shown in FIG. 5 which will be described more completely below.

Anvil 18 is moved with respect to the frame and nosepiece using an anvil translation operator means 83. The anvil translation operator includes a rotatable knurled nut 84 which is held within opening 85 of tailpiece 25. The tailpiece spans across opening 85 using bridges 86, shown in FIGS. 1 and 4.

Nut 84 has internal threads 87 which coact with external threads 88 on the anvil connection means 48. As nut 84 is turned the anvil connection means translates upwardly or downwardly through the frame 22. Movement of anvil 18 with respect to nosepiece 20 allows the anvil to be either expanded or collapsed. The anvil and anvil connection means are prevented from rotating by an anti-rotation pin 89 which extends into slot 90 formed in the side of anvil connection means 48 at some suitable location.

Nosepiece 20 is moved relative to the frame and anvil using a nosepiece translation operator means 96. The nosepiece translation operator includes an operator cylinder 97 having internal threads 98 formed therein. The hollow tubular catheter guide 47 or other nosepiece connection means is provided with external threads 99 which coact with internal threads 98 in operator cylinder 97. Operator cylinder 97 is also provided with a flange 101 which positions the cylinder in tailpiece 25. An anti-rotation means such as anti-rotation pin 110 extends in front of flange 101 to limit the forward motion of operator cylinder 97. Anti-rotation pin 110 also extends into slot 112 in the nosepiece connection means 47 to prevent rotation thereof.

FIG. 4 shows the relative cross-sectional positions of tailpiece 25, not 84, anvil connection means 48, and the combined nosepiece connection means and catheter guide 47. Catheter passageway 70 extends through catheter guide 47 to allow a catheter to extend therethrough. FIG. 4 also shows bridges 86 for keeping tailpiece 25 as an integral unit while allowing access to nut 84.

FIG. 5 shows a cross-sectional view of the staple end 12 in the context of insertion of the expandable anvil 18 and nosepiece 20 into a patient's body. The staple driver assembly 16 includes an enlarged staple head 17 which is rigidly attached to barrel 23 of frame 22. A staple driver 59 is slidable within the staple head 17 and has a number of driver arms 73 which extend through openings 75 in face piece 74. Staples 77 are held within openings 75 until driven outwardly by the staple driver arms 73 as the attached staple driver 59 is forced forward by staple driver connection means 58. The staples can be held to the ends of staple driver arms 73 by providing the ends of the staple driving arms with concave surfaces which engage and slightly hold the staples thereto.

The various components of the expandable anvil surgical stapler have been described above. The operation of the embodiment shown in FIGS. 1 through 8 will now be described with specific reference to FIGS. 5, 6 and 7.

FIG. 5 shows the staple end 12 of the surgical stapler inserted into the body of a patient. The abdominal wall of the patient is represented by layer 78 and the wall of the hollow organ being operated on is represented by layer 79. The peritoneum is represented by layer 80. Organ wall 79 can represent the wall of the stomach, gall bladder, intestine, colon or other organ.

The surgical procedure begins by first inserting a laparoscope into the peritoneal cavity of the patient so that the physician can remotely observe the subsequent surgical insertion of the parts described below. With the laparoscope in place, the physician then inserts a large tubular needle (not shown), through the patient's abdomen. The needle is then extended into the organ being operated upon at an appropriate point with visual guidance using the laparoscope. The physician then threads a catheter through the tubular needle. The catheter preferably includes one or more inflatable dilators which extended into the hollow organ and can be inflated so that the organ can be pulled up tight against peritoneum 80 using the catheter. With the inflated dilator holding the organ against the peritoneum, the needle originally inserted is removed from the patient's body by threading it off of the catheter. The surgical stapling device of this invention is then threaded onto the catheter by placing catheter passage 70 over the catheter.

Figure 6:
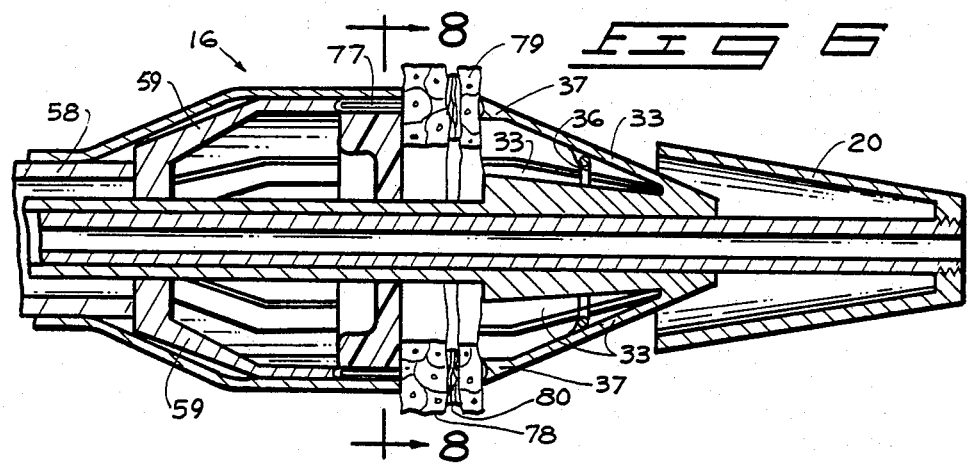
FIG. 6 shows a cross-sectional view similar to FIG. 5 with the anvil expanded and positioned to engage staples.

After the stapler is threaded onto the catheter, the anvil 18 and surrounding nosepiece 20 are extended away from the staple driver assembly 16 using operator cylinder 97 and nut 84, so that the end of the stapler assumes the configuration such as shown in FIG. 5. The anvil 18 and nosepiece 20 are then inserted through the hole formed by the large needle in the abdominal wall 78, peritoneum 80 and organ wall 79 so that they are positioned within the organ. Nut 84 is then rotated to move the anvil 18 back towards the organ wall 79 while simultaneously allowing the anvil struts 33 to expand outwardly. If necessary the nose piece 20 is extended further into the patient's body so that the anvil struts 33 can be fully opened into the extended position shown in FIG. 6. In the extended position the anvil heads 37 are directly opposite from the staples 77 which are to be driven through the abdominal wall 78, peritoneum 80 and organ wall 79. It is preferable that the anvil heads 37 be brought into firm contact with the inside of the organ wall 79, thereby clamping the layers of tissue 78–80 to face piece 74 holding them securely for driving of the staples. FIG. 6 shows such a position for the anvil.

Figure 7:
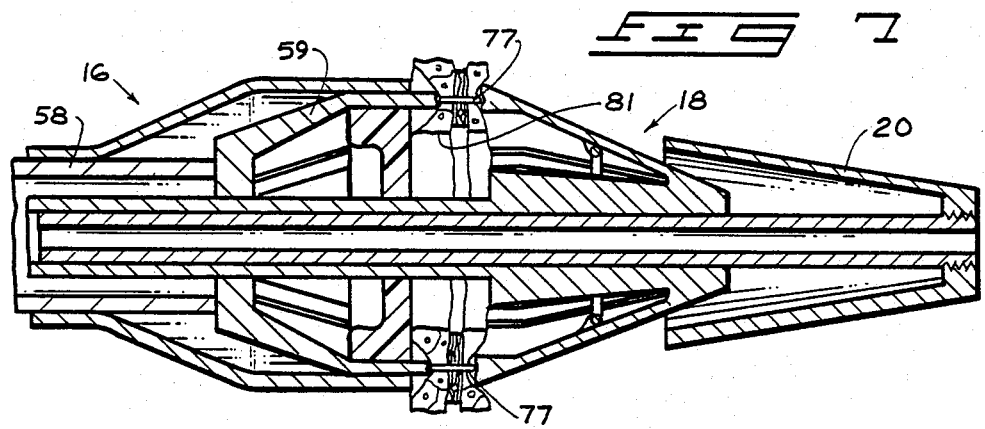
FIG. 7 shows a cross-sectional view similar to FIGS. 5 and 6 with the staples driven through the tissue and crimped by the expanded anvil.

FIG. 7 shows the stapler after staples 77 have been driven through the layers of tissue and have been bent over or crimped when they engage crimping recesses 38 in anvil heads 37. This compresses and securely fastens the three layers of tissue together so that the physician has a very small but relatively durable opening into the patient's body with direct access to the interior of the organ being operated upon. Such a procedure eliminates the need for a large abdominal incision and also the need for a sizable incision into the organ itself.

Once the staples are in place, the physician then turns the nut 84 to release the anvil from the layers of tissue and to move it into the receiving cup 43 of nosepiece 20. As the anvil 18 is driven into the receiving cup 43, the struts 33 are forced into the collapsed position shown in FIG. 5 by grooves 44 on interior surface 45 of the receiving cup. Once the anvil struts are fully collapsed, then it is possible to extract the anvil and nosepiece through the surgical opening 81. The catheter (not shown) is left in plane for further procedures or else removed to allow access into the organ with other surgical tools such as another laparoscope for further examination, cutting instruments or various other surgical tools.

Examples of surgical applications for the invention include: placing a gastrostomy tube in the stomach for supplying nutrition to a patient unable to eat. Access to the stomach interior can also allow the stomach to be decompressed or treated repeatedly by a laser in cases of gastric carcinoma. The invention can also allow for the placement of a cholecystostomy and the extraction and fragmentation of gallstones. Decompression of the right colon via cecostomy can also be accomplished using such procedures. A feeding jejunostomy tube can also be introduced with simultaneous use of an upper endoscope. Many other surgical uses will also be recognized by those skilled in surgical procedures.

The surgical stapler of this invention can be constructed of any number of a variety of materials. Plastics and metals in particular appear suitable for various components as is well known in the art of surgical instrument design.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. A surgical stapler for stapling two or more layers of tissue together, comprising:
   a frame having a staple end and an opposed, handle, end;
   an anvil connected to the end of the frame for slidable motion with respect thereto, the anvil having at least one anvil strut having anvil heads thereon for engaging and bending staples forced against the anvil heads; the anvil struts and anvil heads being movable between a collapsed position wherein the anvil struts and anvil heads are drawn radially inward, and an extended position wherein the anvil heads are extended radially outward to engage and bend staples;
   means for adjustably moving the anvil heads between the collapsed and extended positions; and
   staple driving means adjacent to the anvil for driving staples through layers of tissue and against the anvil heads to crimp the staples and secure the layers of tissue together.

2. The surgical stapler of claim 1 wherein the means for adjustably moving the anvil heads comprises:
   a nosepiece slidably connected to the staple end of the frame, adjacent the anvil; said nosepiece having a receiving cup for engaging the anvil struts to collapse the anvil struts and anvil heads radially inward.

3. The surgical stapler of claim 2 wherein the nosepiece is connected to a nosepiece connection means slidably mounted to the frame and connected to a nosepiece translation operator means for adjustably positioning the nosepiece with respect to the anvil and frame.

4. The surgical stapler of clam 2 wherein the nosepiece is connected to a nosepiece translation operator means for adjustably positioning the nosepiece; and wherein the anvil is connected to an anvil translation operator means for adjustably positioning the anvil.

5. The surgical stapler of claim 4 further defined by a catheter passage extending through the stapler to allow catheters to be inserted and removed therethrough.

6. The surgical stapler of claim 2 wherein the receiving cup has beveled interior surfaces for engaging and collapsing the anvil struts inwardly.

7. The surgical stapler of claim 2 further comprising strut biasing means for expanding the anvil struts and anvil heads outwardly into the extended position when not collapsed inwardly by the receiving cup.

* * * * *